United States Patent [19]

Deuss

[11] Patent Number: 5,049,131
[45] Date of Patent: Sep. 17, 1991

[54] BALLOON CATHETER

[75] Inventor: Jacobus A. C. Deuss, Son en Breugel, Netherlands

[73] Assignee: Ashridge AG, Zug, Switzerland

[21] Appl. No.: 435,724

[22] Filed: Nov. 14, 1989

[30] Foreign Application Priority Data

May 31, 1989 [NL] Netherlands .......................... 8901381

[51] Int. Cl.$^5$ ............................................. A61M 29/00
[52] U.S. Cl. ...................................... 604/96; 604/265; 604/280; 606/194
[58] Field of Search ................. 604/96, 102, 103, 264, 604/280, 265; 606/192, 194; 600/18

[56] References Cited

U.S. PATENT DOCUMENTS

| 4,601,713 | 7/1986 | Fuqua | 604/280 |
|---|---|---|---|
| 4,641,653 | 2/1987 | Rockey | 606/194 |
| 4,681,092 | 7/1987 | Cho et al. | 604/96 |
| 4,710,181 | 12/1987 | Fuqua | 604/280 |
| 4,738,666 | 4/1988 | Fuqua | 604/280 |
| 4,899,747 | 2/1990 | Garren et al. | 604/96 |
| 4,909,252 | 3/1990 | Goldberger | 604/96 |
| 4,917,088 | 4/1990 | Crittenden | 604/96 |

Primary Examiner—Stephen C. Pellegrino
Assistant Examiner—Ralph A. Lewis
Attorney, Agent, or Firm—Wegner, Cantor, Mueller & Player

[57] ABSTRACT

A balloon catheter for the widening of passages in the body, such as blood vessels, comprises a tubular body connected at one side to the interior of a cylindrical balloon and at another side to a pump unit. The balloon can be enlarged from a first predetermined diameter to a second predetermined diameter without completely withdrawing the catheter from the body passages.

12 Claims, 2 Drawing Sheets

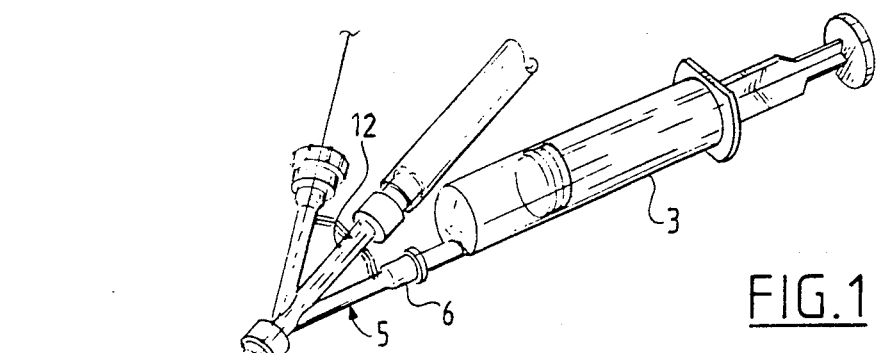
FIG.1
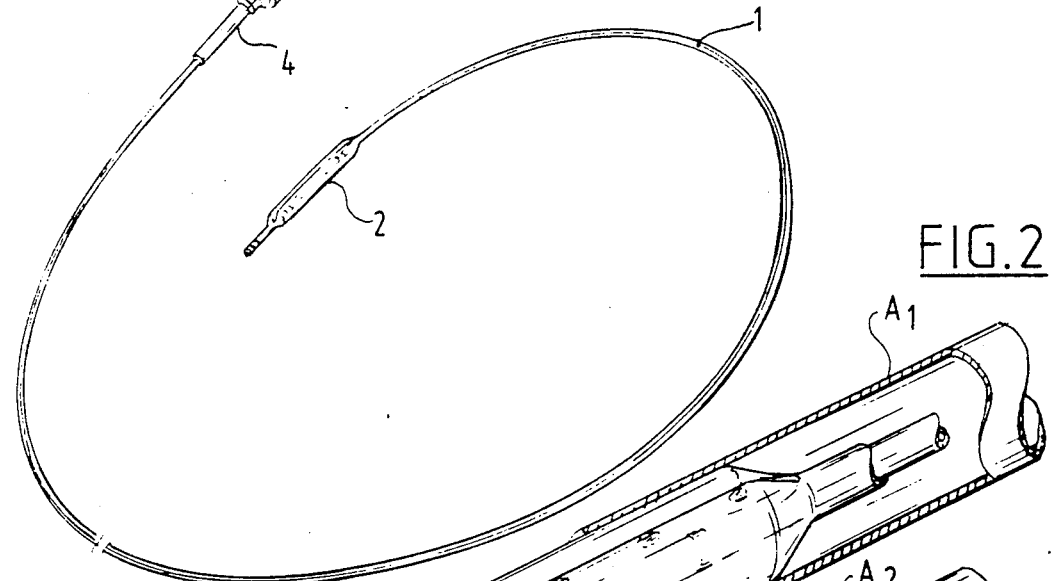
FIG.2
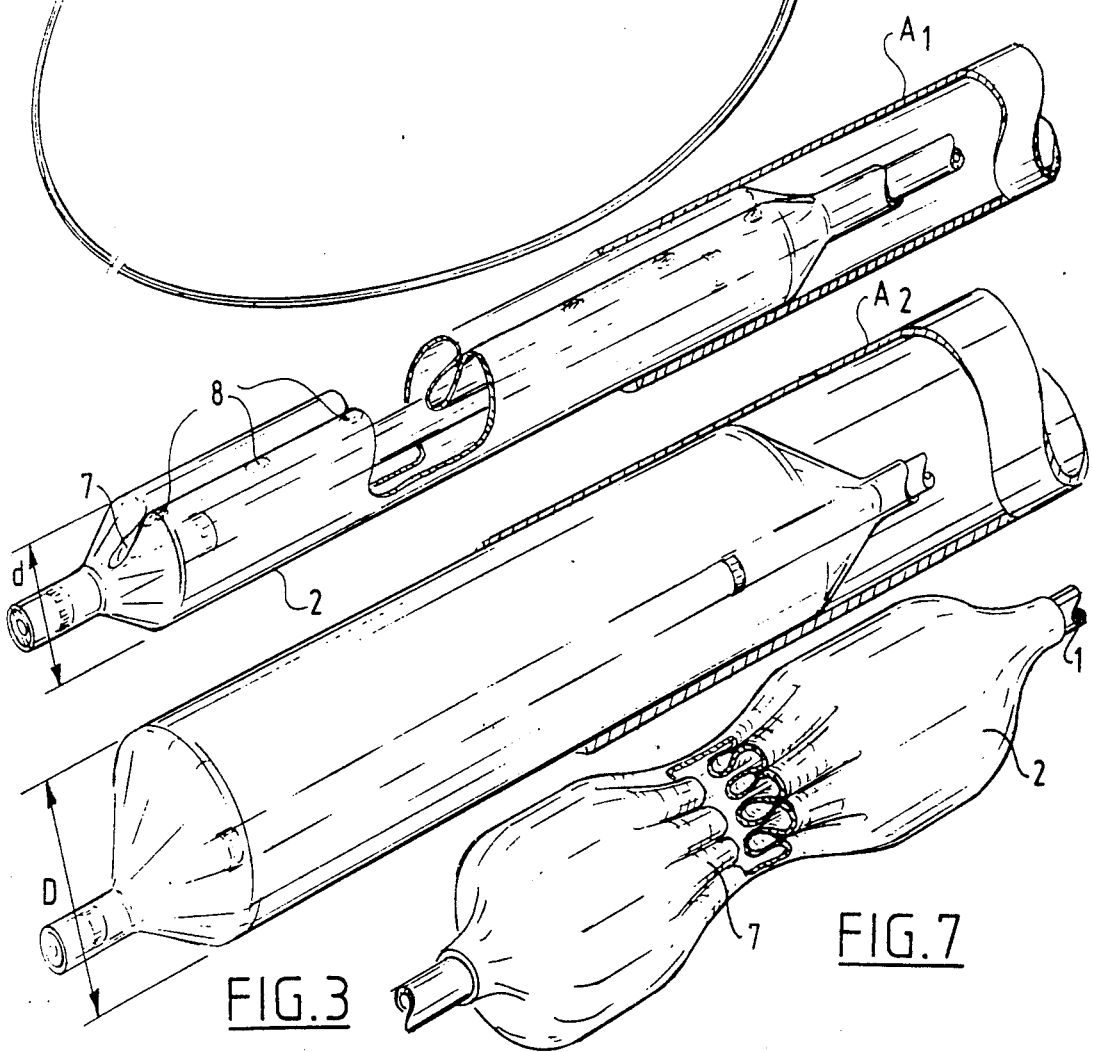
FIG.3
FIG.7

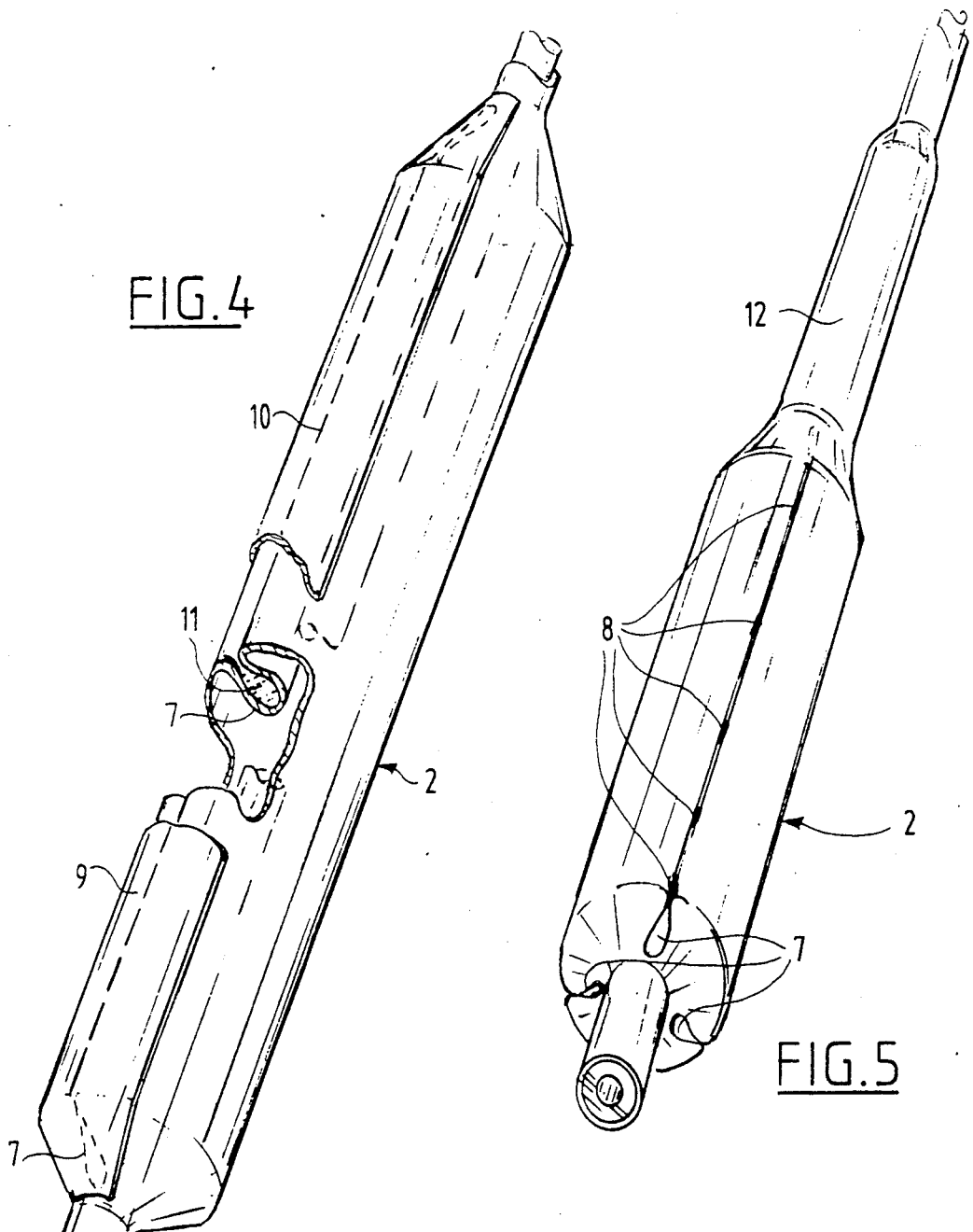
FIG.4
FIG.5
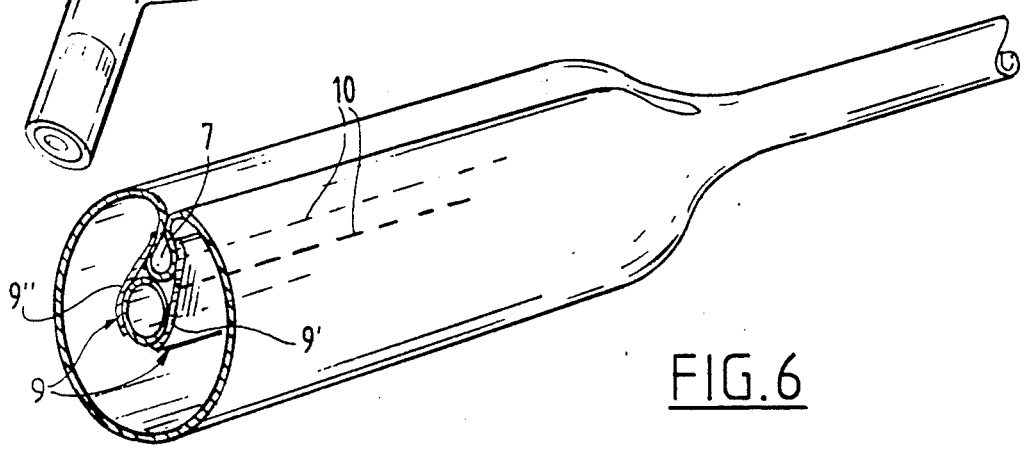
FIG.6

BALLOON CATHETER

BACKGROUND OF THE INVENTION

The invention relates to a balloon catheter for the widening of passages in the human body, for instance blood vessels, consisting of a tubular body which is connected on one side to the interior of a cylindrical balloon of predetermined length and operational diameter, and on the other side to a pump unit for inflation of the balloon with a medium.

Balloon catheters of the type described in the preamble have developed enormously with the use of the so-called angioplasty method, whereby the catheter is inserted intra-vascularly with the end of the balloon, far enough until the balloon arrives at the location for widening of the passage. The balloon is inserted in a deflated state and is inflated in situ at the place for widening by the introduction of a determined medium under pressure, so that the balloon acquires its predetermined diameter. This diameter is determined for each balloon and will not be exceeded by the balloon. The balloon and therefore the catheter is suitable for a determined location, and if during the same operation a second location of a different diameter must be treated, a new catheter has to be inserted. This is time consuming and very expensive.

SUMMARY OF THE INVENTION

The invention has for its object to obviate the above stated drawback and provides for this purpose a balloon catheter which is distinguished in that one or more portions of the cylindrical balloon wall are provided with fixing means such that a wall strip extending lengthwise is turned inward to effect a first operational diameter, and which fixing means are arranged such that they become detached at a determined limit of pressure in the inflating medium in order to bring about a second larger operational diameter.

With the balloon catheter according to the invention a balloon of two or more stages is obtained whereby the starting point is a minimum balloon diameter which is enlarged stepwise each time a determined pressure is exceeded. The surgeon therefore has the opportunity to adjust to a following working area by raising the pressure, so that beginning with the smallest diameter he can draw back the catheter from the smallest blood vessels to larger blood vessels and perform work there. This considerably reduces the necessary operating time as well as the costs related thereto.

In one embodiment the catheter according to the invention is provided with fixing means formed by one or more fixing welds between describing lines of parallel axis located at a distance from each other on the cylindrical wall.

According to another embodiment the fixing means are formed by a fixing strip arranged on the cylinder wall and having one or more weakened points. As the pressure is raised the weakened spots will detach, so that the catheter balloon can be brought from the small to the large diameter. The invention will be further elucidated in the following figure description with reference to a number of embodiments.

BRIEF DESCRIPTION OF THE DRAWINGS

FIG. 1 shows a schematic view of a balloon catheter provided with a balloon according to the invention, FIGS. 2 and 3 each show a perspective top-view of the balloon used with the catheter from FIG. 1, with a narrow and a wide passage, respectively, FIGS. 4 and 5 each show a perspective top view of two embodiment variants, FIG. 6 is a further variant of the invention, FIG. 7 is a longitudinal sectional view and side view of a further variant of the invention having stepped portions with smaller and larger outer diameters.

DESCRIPTION OF THE PREFERRED EMBODIMENTS

The catheter according to the invention consists of a tubular body 1 which is connected on the one side to the interior space of a balloon-shaped body 2 and on the other side to a pump unit 3. To this end the rear end 4 of the tube 1 is arranged airtightly in a branch piece 5 that has three branches. The one branch 6 is connected to the pump unit 3. The second branch 12 connects onto a second tubular body arranged in the tubular body, which second tubular body extends beyond the balloon 2 and serves for the passage of a flexible guide wire, which is pre-arranged in the passages in the human body, for example the blood vessel. The tubular bodies of the catheter are finally carried along this guiding.

The manner of operation of the catheter is assumed to be known and consequently falls outside the scope of the invention.

If the balloon is brought to the location to be treated in the artery $A_1$, see FIG. 2, the balloon can be inflated via the tube 1 to an operational diameter d by the medium in the pump unit 3. In the case that there is a narrowing of the artery $A_1$, the inner diameter of which coincides with the outer diameter of the balloon d, this narrowing can be pressed out. This so-called angioplasty method is also assumed to be known and will not be further described.

The diameter d of the balloon 2 is always of the same size irrespective of the pressure in the balloon 2, which is realized by the use of non-stretch material in the peripheral direction of the cylinder wall.

In the embodiment according to FIGS. 2 and 3, the balloon 2 is formed with a fold 7, which is achieved by fixing to one another at fixing points 8 two describing lines running on a parallel axis. These fixing points can be of any random shape and length as long as care is taken that the outer periphery of the cylinder 2 is virtually circular.

The fixing welds 8 can be detached by raising the pressure, as a result of which the attachment between the two describing lines of the cylinder wall is released, and the balloon can be further inflated to the position as in FIG. 3. In this position the balloon has a diameter D and is suitable for a larger artery $A_2$. It will be apparent from the above that the surgeon will first have to treat the small artery $A_1$ and then the larger artery $A_2$. The surgeon does not therefore need to completely withdraw the catheter from the blood vessel as is usual with existing catheters.

FIG. 4 shows an embodiment, in which the cylindrical wall of the balloon 2 is taken in to form a fold 7, which is realized by arranging a tear-off strip 9 over the balloon. This tear-off strip is provided at line 10 with weakened points, which tear loose when the pressure in the balloon 2 is increased.

The fold 7 can be filled with a substance 11, for example paste, which has a therapeutic or medicinal effect.

This substance is released against the inner wall of the blood vessel as soon as the tear-off strip 9 is torn loose.

For the sake of completeness it is mentioned that the strip 9 is extended over the head end sides of the balloon in order to seal the ends of the fold.

FIG. 5 shows an embodiment in which the balloon 2 displays three folds 7 whereby the weakened areas 8 on each fold 7 have a different release moment, depending on the pressure prevailing in the balloon 2. In this way the balloon can be brought to four different diameters.

It is noted that in FIG. 5 the balloon in inflated state can be stepped in diameter over its length whereby the portions of greater diameter can be provided with the folds 7. In this way a portion 12 can also be applied with a very small diameter, which allows no fold forming.

FIG. 6 shows an embodiment, in which the tear-off strip 9 is arranged in the balloon such that the fold 7 is connected to the coaxial inner tube by means of a tear-off strip 9' and/or 9". Weakened points on the line 10 ensure that when the pressure is raised the strip 9 tears along the line 10, after which the balloon can be further inflated to the larger diameter D.

FIG. 7 shows an embodiment in which a middle portion of a continuous balloon is narrowed by means of the fold(s) 7, here extending in an axial way. The smaller middle section is intended to be located where an accurate position is necessary. For instance, for some heart diseases a valve should be dilated. However, positioning is very difficult due to the high blood velocity therethrough. Owing to the diminished diameter the middle portion can be accurately positioned by fitting it in the narrowed opening in the valve. Afterwards, by raising the pressure in the balloon, the middle portion is brought to the larger diameter of the balloon, so being able to dilate the valve tissue.

The invention is not limited to the embodiments described above.

I claim:

1. A balloon catheter for the widening of passages in the human body comprising:
    an inflatable balloon having a predetermined length and comprising means for widening a passage in the body to a first operational diameter and widening a passage in the body to a larger operational diameter; and
    pump means for delivering an inflating medium to said balloon, said pump means in connection with said balloon through a tubular body connected at one end thereof to said pump means and at a distal end thereof to said balloon;
    said means for widening comprising a portion of an outer wall of the balloon, said portion having an inward fold therein, and means for fixing said inward fold in said portion of the outer wall until a predetermined pressure is reached in said balloon whereby said means for fixing releases said inward fold;
    the portion of said outer wall with said inward fold having a substantially cylindrical shape with an outer diameter corresponding to said first operational diameter, and said portion of said outer wall after release of said inward fold has a substantially cylindrical shape with an outer diameter corresponding to said larger operational diameter.

2. The balloon catheter of claim 1, wherein said inward fold extends longitudinally along said balloon.

3. The balloon catheter of claim 2, wherein said means for fixing comprises a series of releasable welds located within said inward fold on an outer surface of said outer wall.

4. The balloon catheter of claim 1, wherein said means for fixing comprises a releasable weld located within said inward fold on an outer surface of said outer wall.

5. The balloon catheter of claim 1, wherein said means for fixing comprises a releasable strip attached to an inner surface of the portion of the outer wall containing said inward fold.

6. The balloon catheter of claim 1, wherein said means for fixing comprises a releasable strip attached to an outer surface of the portion of the outer wall containing said inward fold.

7. The balloon catheter of claim 6, wherein said releasable strip extends over ends of the balloon and the inward fold is filled with a substance.

8. The balloon catheter of claim 7, wherein said substance is a medicinal substance.

9. The balloon catheter of claim 1, wherein said portion of the outer wall comprises a plurality of inward folds therein and said balloon comprises corresponding means for fixing said inward folds in said outer wall, wherein each of said means for fixing releases a corresponding inward fold when a different predetermined pressure is reached in said balloon.

10. The balloon catheter of claim 9, wherein each of said inward folds extends longitudinally along said balloon.

11. The balloon catheter of claim 1, wherein said inward fold extends longitudinally along substantially an entire length of said balloon.

12. The balloon catheter of claim 1, wherein said inward fold extends longitudinally along only a portion of a length of said balloon.

* * * * *